United States Patent [19]

Beck et al.

[11] 4,402,732
[45] Sep. 6, 1983

[54] HERBICIDALLY ACTIVE DIHALOGENATED IMIDAZOLECARBOXYLIC ACID AMIDES, COMPOSITIONS AND USE

[75] Inventors: Gunther Beck; Bernd Baasner; Ludwig Eue, all of Leverkusen; Robert Schmidt, Bergisch-Gladbach, all of Fed. Rep. of Germany

[73] Assignee: Bayer Aktiengesellschaft, Leverkusen, Fed. Rep. of Germany

[21] Appl. No.: 341,038

[22] Filed: Jan. 20, 1982

[30] Foreign Application Priority Data

Feb. 11, 1981 [DE] Fed. Rep. of Germany ....... 3104759

[51] Int. Cl.³ .................... A01N 43/50; C07D 233/04
[52] U.S. Cl. ......................................... 71/92; 548/337
[58] Field of Search ............................ 548/337; 71/92

[56] References Cited

U.S. PATENT DOCUMENTS 4,179,277 12/1979 Beck et al. ................. 71/92

FOREIGN PATENT DOCUMENTS 2610527 9/1977 Fed. Rep. of Germany .

*Primary Examiner*—Robert W. Ramsuer
*Attorney, Agent, or Firm*—Sprung, Horn, Kramer & Woods

[57] ABSTRACT

A dihalo-imidazolecarboxylic acid amide of the formula

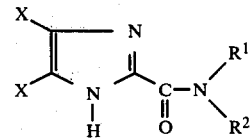

in which
  X each independently is chlorine or bromine,
  $R^1$ is fluoroalkyl or fluorochloroalkyl, and
  $R^2$ is hydrogen or alkyl which possesses herbicidal activity and novel intermediates there

13 Claims, No Drawings

HERBICIDALLY ACTIVE DIHALOGENATED IMIDAZOLECARBOXYLIC ACID AMIDES, COMPOSITIONS AND USE

The present invention relates to certain new dihalogenated imidazolecarboxylic acid amides, to a process for their preparation and to their use as herbicides.

It has already been disclosed that certain 4,5-dichloroimidazole-2-carboxylic acid derivatives possess herbicidal properties (see U.S. Pat. No. 4,179,277). Thus, for example, 4,5-dichloroimidazole-2-carboxylic acid tert.-butylamide can be employed for combating weeds. This compound is, however, not always adequately active and its selectivity is not always entirely satisfactory.

The present invention now provides, as new compounds, the dihalogenated imidazolecarboxylic acid amides of the general formula

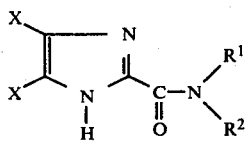

in which
X represents chlorine or bromine,
$R^1$ represents fluoroalkyl or fluorochloroalkyl and
$R^2$ represents hydrogen or alkyl.

The present invention also provides a process for the preparation of a dihalogenated imidazolecarboxylic acid amide of the formula (I) in which
(a) the dimeric ketone of the formula

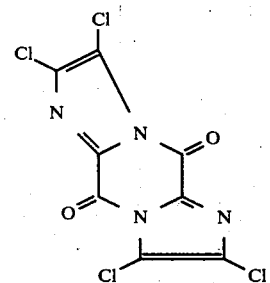

is reacted with a fluorinated amine of the general formula

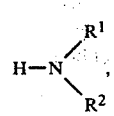

in which
$R^1$ and $R^2$ have the abovementioned meanings,
if appropriate in the presence of a diluent and, if appropriate, in the presence of a catalyst, or (b) an imidazole-2-carboxylic acid amide of the general formula

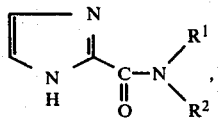

in which
$R^1$ and $R^2$ have the abovementioned meanings,
is reacted with at least the amount of chlorinating agent or brominating agent stoichiometrically required for the dihalogenation, in the presence of a diluent which is inert under the reaction conditions and, if appropriate, in the presence of an acid-binding agent, or (c) perchlorodiazafulvene of the formula

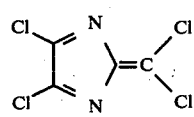

is reacted with a fluorinated amine of the general formula

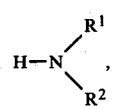

in which
$R^1$ and $R^2$ have the abovementioned meanings,
in the presence of a diluent and, if appropriate, in the presence of an acid-binding agent, and the product is then hydrolyzed with water.

It has been found that the dihalogenated imidazolecarboxylic acid amides of the formula (I) possess powerful herbicidal, in particular also selectively herbicidal, properties.

Surprisingly, the dihalogenated imidazolecarboxylic acid amides according to the invention, while having a very good action against weeds, in particular exhibit better possibilities of use as selective weed-combating agents in important crops than does 4,5-dichloroimidazole-2-carboxylic acid tert.-butylamide, known from the prior art, which is a highly effective active compound of similar structure and of the same type of action.

The compounds according to the invention thus represent a valuable enrichment of herbicidal agents for the selective combating of weeds.

The formula (I) provides a general definition of the dihalogenated imidazolecarboxylic acid amides according to the invention. In this formula,
X represents chlorine or bromine,
$R^1$ preferably represents straight-chain or branched fluoroalkyl with 1 to 8 carbon atoms and 1 to 9 fluorine atoms or straight-chain or branched fluorochloroalkyl with 1 to 8 carbon atoms and up to 9 fluorine and chlorine atoms, and
$R^2$ preferably represents hydrogen or alkyl with 1 to 6 carbon atoms.

Particularly preferred compounds of the formula (I) are those in which
X represents chlorine or bromine,
$R^1$ represents straight-chain or branched fluoroalkyl with 1 to 6 carbon atoms and 1 to 7 fluorine atoms or straight-chain or branched fluorochloroalkyl with 1 to 6 carbon atoms and up to 7 fluorine and chlorine atoms, and $R^2$ represents hydrogen or alkyl with 1 to 4 carbon atoms.

If, in process variant (a), the dimeric ketene of the formula (II) and 1-amino-3,3,3-trifluoropropane are used as starting materials, the course of the reaction can be represented by the following equation:

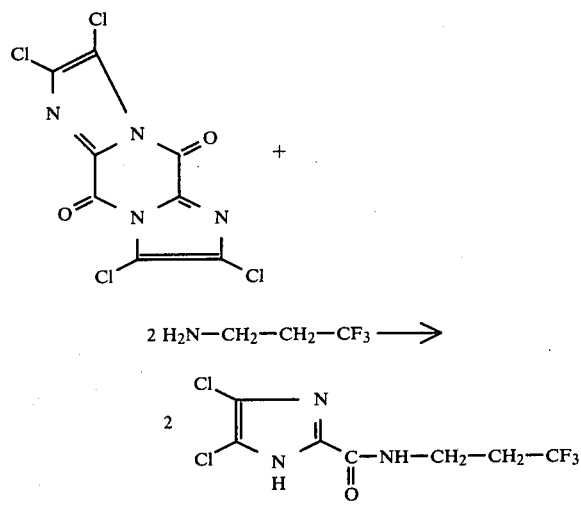

If, in process variant (b), imidazole-2-carboxylic acid N-(2,2,2-trifluoroisopropyl)-amide and bromine are used as starting materials, the course of the reaction can be represented by the following equation:

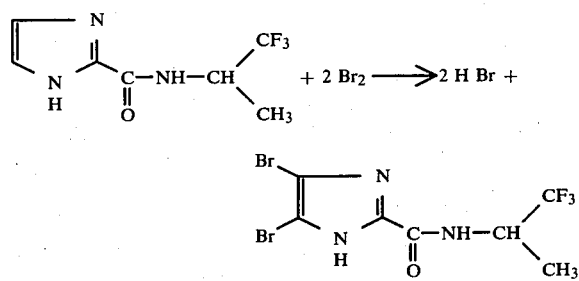

If, in process variant (c), the perchlorodiazafulvene of the formula (V) and 2-amino-1,1,1-trifluoropropane are used as starting materials and water as the hydrolyzing agent, the course of the reaction can be represented by the following equation:

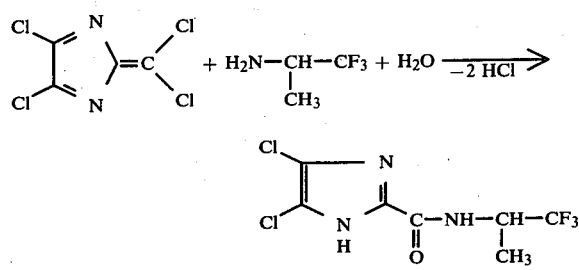

The dimeric ketene of the formula (II) required as a starting material in process variant (a) is known (see DE-A (German Patent Application) No. 2,634,053).

The formula (III) provides a general definition of the fluorinated amines additionally required as starting materials in process variant (a). In this formula, $R^1$ and $R^2$ preferably have those meanings which have already been stated to be preferred in connection with the description of the compounds of the formula (I).

Fluorinated amines of the formula (III) are known (see J. Org. Chem. 24, 1256–1259 (1959), J. Org. Chem. 27, 1406–1409 (1962), J. Med. Chem. 22, 1130–1133 (1979), Izv. Aka. Nauk, SSSR Ser. Khim. 1966, 1518 (in English), U.S. Pat. No. 3,908,012, U.S. Pat. No. 3,960,949 and DE-A (German Patent Application) No. 2,117,015) and can be prepared in accordance with methods which are known in principle. Thus, for example, those fluorinated amines of the general formula

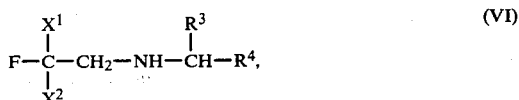

in which
$X_1$ represents hydrogen, fluorine or chlorine,
$X^2$ represents hydrogen, fluorine or chlorine,
$R^3$ represents alkyl and
$R^4$ represents hydrogen or alkyl,
are obtained by hydrogenating fluorinated azomethines of the general formula

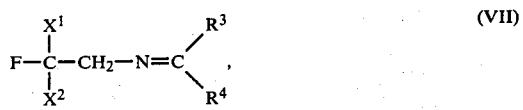

in which
$X^1$, $X^2$, $R^3$ and $R^4$ have the abovementioned meanings,
with hydrogen under a pressure of 3 to 15 bar in the presence of a catalyst, such as platinum on charcoal, palladium on charcoal or Raney nickel, and in the presence of a diluent, for example an alcohol, such as methanol or ethanol, or an ether, such as dioxane, at temperatures between 0° C. and 60° C., preferably between 10° C. and 50° C.

In formula (VI)
$X^1$ preferably represents hydrogen, fluorine or chlorine,
$X^2$ preferably represents hydrogen, fluorine or chlorine,
$R^3$ preferably represents alkyl with 1 to 4 carbon atoms and
$R^4$ preferably represents hydrogen or alkyl with 1 to 4 carbon atoms.

The azomethines of the formula (VII) required as starting materials in the preparation of the fluorinated amines of the formula (VI) in accordance with the process described above have not previously been described in the literature. However, they can be prepared by reacting amines of the general formula

in which
$X^1$ and $X^2$ have the abovementioned meanings, with carbonyl compounds of the general formula

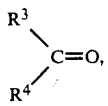 (IX)

in which

R³ and R⁴ have the abovementioned meanings, if appropriate in the presence of a diluent, such as pentane, hexane, cyclohexane, chloroform, carbon tetrachloride, benzene, toluene, xylene, chlorobenzene, diethyl ether, tetrahydrofuran or dioxane, at a temperature between −20° C. and +60° C., preferably between 0° C. and +40° C.

The amines of the formula (VII) and carbonyl compounds of the formula (IX) required as starting materials for the synthesis of the fluorinated azomethines of the formula (VII) in accordance with the above process are known and can be prepared by methods known in principle.

Possible diluents for the reaction in process variant (a) are the fluorinated amines of the formula (III), used as reactants, in themselves, provided they are in the liquid state or melt at low temperatures, and also inert organic solvents. These include, as preferences, chlorinated hydrocarbons, such as methylene chloride and chloroform, as well as ethers, such as diethyl ether, tetrahydrofuran and dioxane. Furthermore, alcohols with 1 to 4 carbon atoms, such as methanol or isopropanol, or even water, can also function as diluents.

Catalysts which can be used in process variant (a) are strong inorganic bases, such as sodium hydroxide or potassium hydroxide, or amines, such as triethylamine or triethylenediamine.

The reaction temperatures in process variant (a) can be varied within a substantial range. In general, the reaction is carried out at temperatures of between −50° C. and +200° C., preferably between 0° C. and 100° C.

In carrying out process variant (a), 2 mols or even a greater excess of fluorinated amine of the formula (III) and, if appropriate, 0.01 to 1, preferably 0.1 to 0.5, mol of catalyst are employed per mol of dimeric ketene of formula (II). The isolation of the dihalogenated imidazolecarboxylic acid amides formed, of the formula (I), is carried out in accordance with customary methods. In general, the procedure followed is that, after completion of the reaction, any solvent and any component (III) present in excess are distilled off and the residue which is left is stirred with an aqueous alkali metal base and then acidified, after which the product which is thereby obtained in a crystalline form is filtered off and is recrystallized, if necessary.

The formula (IV) provides a general definition of the imidazole-2-carboxylic acid amides required as starting materials in process variant (b). In this formula, R¹ and R² preferably have those meanings which have already been mentioned as preferred in connection with the description of the compounds of the formula (I).

The amidazole-2-carboxylic acid amides of the formula (IV) have not previously been described in the literature; they can, however, be prepared according to customary methods. Thus, these compounds are obtained by reacting the dimeric ketene of the formula

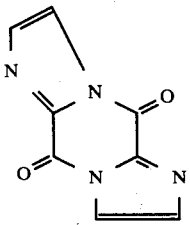 (X)

with fluorinated amines of the general formula

 (III)

in which

R¹ and R² have the abovementioned meanings, if appropriate in the presence of a diluent and, if appropriate, in the presence of a catalyst, at temperatures between −50° C. and +200° C., preferably between 0° C. and +100° C.

The dimeric ketene of the formula (X) required as a starting material in the preparation of the imidazole-2-carboxylic acid amides of the formula (IV) has not previously been described in the literature. However, it can be prepared by heating imidazole-2-carboxylic acid with an excess of thionyl chloride under reflux, if appropriate in the presence of dimethylformamide as a catalyst.

Imidazole-2-carboxylic acid is known (see Acta Chem. Scand. 21 279 (1967)).

In preparing the imidazole-2-carboxylic acid amides of the formula (IV) in accordance with the process described above, possible diluents and possible catalysts are any of those compounds which have been mentioned in this context in the description of process variant (a). The above process is carried out in the same way as described for process variant (a). In working up, customary methods are followed. In general, the procedure employed is that after completion of the reaction, any solvent and any component of the formula (III) present in excess are distilled off and the residue left is then stirred with aqueous hydrochloric acid after which it is rendered alkaline with an aqueous alkali metal base and the product which is thereby obtained in a crystalline form is separated off and is recrystallized if necessary.

Chlorinating agents and brominating agents which can be employed in process variant (b) include the halogens chlorine and bromine, and also chlorine donors, such as sulphuryl chloride.

Preferred acid-binding agents which can be used in process variant (b) are alkali metal or alkaline earth metal hydroxides, carbonates or bicarbonates, for example sodium hydroxide or sodium bicarbonate.

Diluents which can be used in process variant (b) are any of the solvents which are inert under the reaction conditions. These include, as preferences, methylene chloride and chloroform. However, the reaction can also be carried out in an aqueous medium, if appropriate in the presence of an acid acceptor.

The reaction temperatures in process variant (b) can be varied within a substantial range. In general, the reaction is carried out at a temperature of between −50° C. and +150° C., preferably between −20° C. and +100° C. If water is used as the diluent, the reaction is advantageously carried out at between 0° C. and +50° C.

In carrying out process variant (b), 2 mols or even a greater excess, preferably 2.5 mols, of chlorinating agent or brominating agent are employed per mol of imidazole-2-carboxylic acid amide of the formula (IV) and, if water is used as the diluent, two or more equivalents of an acid-binding agent are employed. Preferably, the procedure followed is that the imidazole-2-carboxylic acid amide of the formula (IV), in a diluent, is first taken, and the halogenating agent is then added, if appropriate with cooling, at a rate such that the chosen reaction temperature is maintained. To complete the reaction, the reaction mixture can, after the addition of the halogenating agent has ended, be kept at the chosen temperature for a further 1 to 5 hours. If water is used as the diluent, the acid acceptor can either be initially introduced with the imidazole-2-carboxylic acid amide of the formula (IV) or be added after addition of the halogenating agent. The simultaneous addition of acid acceptor and halogenating agent is also possible. In another procedure it is also possible first to take the halogenating agent and then to add a solution of the imidazole-2-carboxylic acid amide of the formula (IV).

The reaction products are isolated in accordance with customary methods. In general, the procedure followed is that if inert organic solvents are used as diluents, the latter are stripped off after completion of the reaction and the residue is purified, if necessary, by treating the crude product with aqueous hydrochloric acid in a ratio of 1:1, at 20° C. This dissolves monohalogenated compounds and non-halogenated starting material, while the dihalogenated product remains in solid form and can be filtered off. If the reaction is carried out in the presence of water as a diluent, working up is in general effected by rendering the reaction mixture alkaline by adding an aqueous alkali metal base, separating off the product which has precipitated, washing it and, if necessary, recrystallizing it.

The perchlorodiazafulvene of the formula (V) required as a starting material in process variant (c) is already known (see DE-A (German Patent Application) No. 2,454,326).

Diluents which can be used in the reaction in process variant (c) are the fluorinated amines of the formula (III), used as reactants, in themselves—provided they are in the liquid state or melt at low temperatures—as well as inert organic solvents. These include, as preferences, ethers, such as dioxane or tetrahydrofuran, or aliphatic nitriles, such as acetonitrile. However, water can also be used.

Acid-binding agents which can be used in process variant (c) are any of the customary acid acceptors. Preferred acid acceptors are alkali metal or alkaline earth metal hydroxides, carbonates or bicarbonates, for example sodium hydroxide or sodium bicarbonate.

The reaction temperatures in process variant (c) can be varied within a substantial range. In general, the reaction is carried out at a temperature of between 0° C. and 150° C., preferably between 20° C. and 100° C.

In carrying out the process variant (c), 1 mol or even a greater excess of fluorinated amine of the formula (III) and, if appropriate, 2 mols or even a greater excess of acid-binding agent are employed per mol of perchlorodiazafulvene of the formula (V). Working up is effected in accordance with customary methods. In general, the procedure followed is that after completion of the reaction any diluent and any compound of the formula (III) present in excess are distilled off, the residue which is left is stirred with water and the product which is thereby obtained in a crystalline form is separated off and, if necessary, is purified by recrystallization or sublimation.

The active compounds according to the invention influence plant growth and can therefore be used as defoliants, desiccants, agents for destroying broad-leaved plants and germination inhibitors, and especially as weedkillers. By "weeds", in the broadest sense, there are to be understood all plants which grow in locations where they are undesired. Whether the substances according to the invention act as total or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The substances according to the invention are particularly suitable for selectively combating weeds in corn and cereals (for example wheat and oats).

The active compounds can be converted into the customary formulations, such as solutions, emulsions, suspensions, powders, foams, pastes, granules, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol esters, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with other herbicides, finished formulations or tank mixing being possible. Mixtures with other active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders and granules. They may be used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.05 and 10 kg of active compound per hectare, preferably between 0.1 and 5 kg/ha.

The present invention also provides a herbicidal composition containing as active ingredient a compound of the present invention in admixture with a solid diluent or carrier or in admixture with a liquid diluent or carrier containing a surface-active agent. The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Preparation of Starting Materials

Example 1

$$CF_3-CH_2-N=CH-CH_3 \qquad \text{(VII-1)}$$

44 g (1 mol) of freshly distilled acetaldehyde were added dropwise in the course of 60 minutes to 90 g (1 mol) of 2,2,2-trifluoroethylamine, while cooling with ice. Stirring was continued for 1 hour, 15 g of solid potassium hydroxide were added and the phases were separated. The organic phase was dried over about 5 g of solid potassium hydroxide and was then distilled through a column. After first runnings (20 g; boiling point 18°–42° C.), consisting of unconverted amine and acetaldehyde, 77.5 g (62% of theory) of ethylidene-2,2,2-trifluoroethyl-amine were obtained.

Boiling point = 73°–74° C.

$n_D^{20} = 1.3415$.

The following fluorinated azomethines were obtained by analogous methods:

$$CF_3-CH_2-N=CH-CH_2-CH_3 \qquad \text{(VII-2)}$$

Yield: 64% of theory.
Boiling point = 93°–95° C.

$$CF_3-CH_2-N=CH_2-CH_2-CH_2-CH_3 \qquad \text{(VII-3)}$$

Yield: 72% of theory.
Boiling point = 116°–118° C.

Example 2

(III-1)

125 g (1 mol) of ethylidene-2,2,2-trifluoroethylamine were dissolved in 250 ml of absolute ethanol, 4 g of 5% strength platinum on charcoal were added and hydrogenation was carried out at 30° C. under a hydrogen pressure of 10 bar for 90 minutes. After filtering off the catalyst, the filtrate was acidified with concentrated hydrochloric acid and evaporated to dryness under reduced pressure. The product thereby obtained was mixed with 100 ml of 50% strength aqueous sodium hydroxide solution and distilled. In this way, 83 g (65% of theory) of 2,2,2-trifluoro-ethyl N-ethylamine were obtained.

Boiling point = 61°–62° C.

$n_D^{20} = 1.3335$.

The following fluorinated amines were obtained by analogous methods:

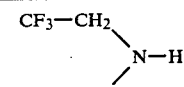

(III-2)
Yield: 66% of theory
$n_D^{20} = 1.3462$
Boiling point = 74° C.

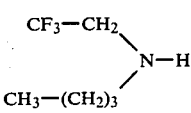

(III-3)
Yield: 72% of theory
$n_D^{20} = 1.3590$
Boiling point = 84° C.

Example 3

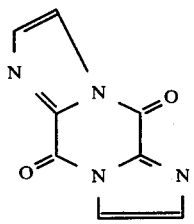

Variant α

11.2 g (0.1 mol) of imidazole-2-carboxylic acid were stirred with 100 ml of thionyl chloride under reflux for 5 hours. After the mixture had cooled, the product was filtered off, washed with a small amount of petroleum ether and dried. This gave 5H,10H-diimide-azo-[1,2-a:1',2'-d]pyrazine-5,10-dione in the form of a yellow powder, in almost quantitative yield. The substance did not melt below 290° C. It could be sublimed without decomposition at 200°–250° C./0.01 mm Hg to give yellow crystals. IR (KBr): 3137, 1735, 1522, 1445, 1387, 1331, 1274, 1161, 1059, 1018, 810, 800, 748, 699 and 651 cm$^{-1}$.

Variant β

The procedure described under (α) was followed with the difference that 1 ml of dimethylformamide was added. The reaction to give the compound of the formula

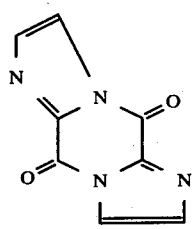

(X)

was virtually complete after only about half an hour, as shown by comparison of the IR spectra.

Example 4

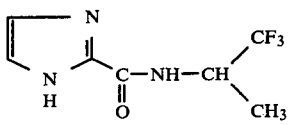

18.8 g (0.1 mol) of dimeric ketene of the formula

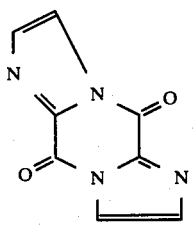

were stirred into a mixture of 24.37 g (0.22 mol) of 2-amino-1,1,1-trifluoropropane and 200 ml of water at room temperature. After stirring for a further four hours at room temperature, the yellow color of the dimeric ketene had disappeared. The mixture was then concentrated on a rotary evaporator in vacuo, the residue was stirred with 500 ml of 1 N hydrochloric acid, slight amounts of impurities were filtered off and the pH value was brought to 6 with aqueous sodium hydroxide solution. After filtering off the product, washing it with water and drying it, 22.15 g (54% of theory) of imidazole-2-carboxylic acid N-(2,2,2-trifluoro-isopropyl)-amide of melting point 234° C. were obtained. The product could be recrystallized from acetonitrile.

PREPARATION OF END PRODUCTS

Example 5

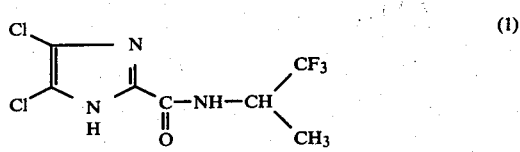

(1)

A solution of 21.6 g (0.099 mol) of perchlorodiazafulvene, of the formula

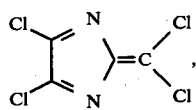

in 50 ml of dioxane was added dropwise to 12.39 g (0.11 mol) of 2-amino-1,1,1-trifluoropropane in 100 ml of dioxane at room temperature, with cooling. After heating for two hours under reflux, the mixture was cooled and concentrated to dryness on a rotary evaporator in a waterpump vacuum, the residue was stirred with water and the product was filtered. After washing the product with water and drying it, 24.8 g (90.7% of theory) of 4,5-dichloroimidazole-2-carboxylic acid N-(2,2,2-trifluoro-ispropyl)amide were obtained. Melting point 160° C. (from hexane). The compound could be sublimed at 125° C./0.05 mm Hg.

The compounds indicated in terms of their formula in the table which follows were also prepared by analogous methods:

TABLE 1

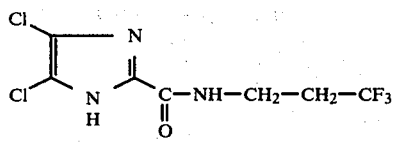
(Ia)

| Compound No. | R¹ | R² | Melting point in °C. | Recrystallized from |
|---|---|---|---|---|
| 2 | —CH$_2$—CF$_2$—CH$_3$ | H | 204 | small amount of acetonitrile |
| 3 | —CH$_2$—CF$_3$ | H | 180 | acetonitrile |
| 4 | —CH$_2$—CF$_3$ | —CH$_2$—CH$_3$ | 122 | petroleum ether |
| 5 | —CH$_2$—CH$_2$—CCl$_2$F | H | 150 | cyclohexane |

Example 6

(6)

11.2 g (0.1 mol) of triethylenediamine, of the formula

, followed by 11.3 g (0.1 mol) of 1-amino-3,3,3-trifluoropropane were added, at room temperature, to a suspension of 13.6 g (0.042 mol) of the dimeric ketene of the formula

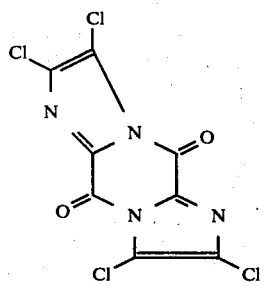

in 130 ml of dioxane. After having been heated under reflux for one hour, the mixture was cooled and evaporated to dryness on a rotary evaporator in a waterpump vacuum, the residue was stirred with 100 ml of 20% strength aqueous sodium hydroxide solution and the mixture was then acidified to pH=1 with hydrochloric acid. After filtering off, washing with water and drying, 19.0 g (corresponding to 81.9% of theory) of 4,5-dichloroimidazole-2-carboxylic acid N-(3,3,3-trifluoro-n-propyl)-amide were obtained. Melting point 177° C. (from acetonitrile).

Example 7

(7)

25.6 g (0.16 mol) of bromine were added dropwise in the course of about one hour to a suspension of 14.5 g (0.07 mol) of imidazole-2-carboxylic acid N-(2,2,2-trifluoro-isopropyl)-amide in 150 ml of water at 0°–10° C., while cooling with ice. After stirring for a further three hours, the pH was adjusted to 6 by dropwise addition of aqueous 1 N sodium hydroxide solution and the product was filtered off, washed with water and dried. 16.0 g (corresponding to 62% of theory) of 4,5-dibromoimidazole-2-carboxylic acid N-(2,2,2-trifluoro-isopropyl)-amide were obtained. After recrystallization from a small amount of acetonitrile, fine needles of melting point 185° C. were obtained.

Example 8

Formulation

For the preparation of a wettable powder
- 70 parts by weight of the active compound according to Example 5
- 2 parts by weight of a surface-active agent
- 3 parts by weight of a dispersing agent on basis of ligninsulfonate
- 5 parts by weight of alkylarylsulfonate
- 5 parts by weight of highly-dispersed silicic acid
- 15 parts by weight of kaolin were thoroughly mixed in a Lödige mixer and then were finely ground in a Mikronizer 8". Before applying the resulting powder to the plants, it was mixed with the desired amount of water.

Use Examples

The herbicidal activity of the compounds of this invention is illustrated by the following examples wherein the compounds according to the present invention are each identified by the number (given in brackets) from the preparative examples hereinabove:

The following compound of the prior art was used for comparison purposes.

(A) = 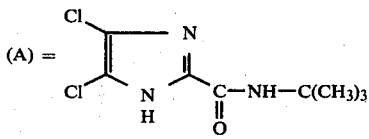

(4,5-Dichloroimidazole-2-carboxylic acid tert.-butylamide)

Example 9

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

In this test, active compounds (3), (4) and (6) according to the invention showed a better activity than comparison substance (A).

Example 10

Post-emergence test/greenhouse
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate is diluted with water to the desired concentration.

Test plants which had a height of 5–15 cm were sprayed with the preparation of the active compound in such a way as to apply prescribed amounts of active compound per unit area. The concentration of the spray liquor was so chosen that the prescribed amounts of active compound were applied in 2,000 liters of water/ha. After three weeks, the degree of damage to the plants was rated in % damage in comparison to the development of the untreated control. The figures denoted:

0% = no action (like untreated control)
100% = total destruction

In this test, active compounds (3) and (6) according to the invention showed a better activity than comparison substance (A).

It will be understood that the specification and examples are illustrative but not limitative of the present invention and that other embodiments within the spirit and scope of the invention will suggest themselves to those skilled in the art.

What is claimed is:

1. A dihalo-imidazolecarboxylic acid amide of the formula

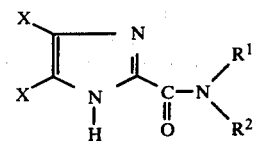

in which
X each independently is chlorine or bromine,
$R^1$ is fluoroalkyl or fluorochloroalkyl, and
$R^2$ is hydrogen or alkyl.

2. A compound according to claim 1, in which
$R^1$ is fluoroalkyl with 1 to 8 carbon atoms and 1 to 9 fluorine atoms or fluorochloroalkyl with 1 to 8 carbon atoms and up to 9 fluorine and chlorine atoms, and
$R^2$ is hydrogen or alkyl with 1 to 6 carbon atoms.

3. A compound according to claim 1, in which
$R^1$ is fluoroalkyl with 1 to 6 carbon atoms and 1 to 7 fluorine atoms or fluorochloroalkyl with 1 to 6 carbon atoms, and
$R^2$ is hydrogen or alkyl with 1 to 4 carbon atoms.

4. A compound according to claim 1, wherein such compound is 4,5-dichloroimidazole-2-carboxylic acid N-(2,2,2-trifluoro-isopropyl)-amide of the formula

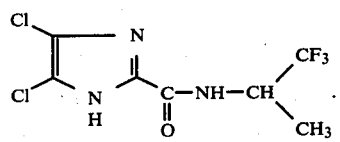

5. A compound according to claim 1, wherein such compound is 4,5-dichloroimidazole-2-carboxylic acid N-(2,2-difluoropropyl)-amide of the formula

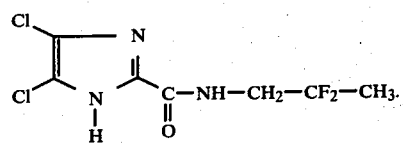

6. A compound according to claim 1, wherein such compound is 4,5-dichloroimidazole-2-carboxylic acid N-(2,2,2-trifluoroethyl)-amide of the formula

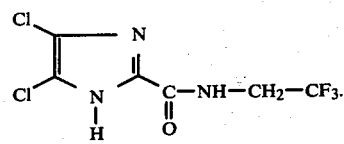

7. A compound according to claim 1, wherein such compound is 4,5-dichloroimidazole-2-carboxylic acid N-(3,3,3-trifluoropropyl)-amide of the formula

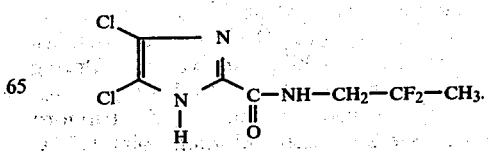

8. A compound according to claim 1, wherein such compound is 4,5-dibromoimidazole-2-carboxylic acid N-(2,2,2-trifluoro-isopropyl)-amide of the formula

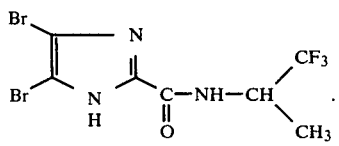

9. A herbicidal composition comprising a herbicidally effective amount of a compound according to claim 1 in admixture with a diluent.

10. A method of combating weeds comprising applying to the weeds, or to a habitat thereof, a herbicidally effective amount of a compound according to claim 1.

11. The method of claim 10 wherein such compound is
 4,5-dichloroimidazole-2-carboxylic acid N-(2,2,2-trifluoro-isopropyl)-amide,
 4,5-dichloroimidazole-2-carboxylic acid N-(2,2-difluoropropyl)-amide,
 4,5-dichloroimidazole-2-carboxylic acid N-(2,2,2-trifluoroethyl)-amide,
 4,5-dichloroimidazole-2-carboxylic acid N-(3,3,3-trifluoropropyl)-amide or
 4,5-dibromoimidazole-2-carboxylic acid N-(2,2,2-trifluoro-isopropyl)amide.

12. An imidazole-2-carboxylic acid amide of the formula

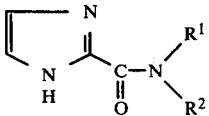

in which
 $R^1$ is fluoroalkyl or fluorochloroalkyl, and
 $R^2$ is hydrogen or alkyl.

13. A fluorinated amine of the formula

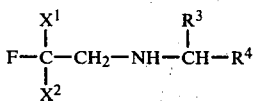

in which
 $X^1$ is hydrogen, fluorine or chlorine,
 $X^2$ is hydrogen, fluorine or chlorine,
 $R^3$ is alkyl and
 $R^4$ is hydrogen or alkyl.

* * * * *